(12) United States Patent
Andresen et al.

(10) Patent No.: US 8,404,190 B2
(45) Date of Patent: Mar. 26, 2013

(54) HYDROCARBON/OXYGEN INDUSTRIAL GAS MIXER WITH WATER MIST

(75) Inventors: Harvey E. Andresen, Luling, LA (US); Christopher P. Christenson, Lake Jackson, TX (US); Charles W. Lipp, Lake Jackson, TX (US); John R. Mayer, The Woodlands, TX (US); Thomas J. Kling, Midland, MI (US); Victor R. Fey, West Bloomfield, MI (US); Laurence G. Britton, Charleston, WV (US); Michael J. Rangitsch, Saginaw, MI (US); Michael L. Hutchison, Poca, WV (US)

(73) Assignee: Dow Technology Investments LLC, Midland, MI (US)

( * ) Notice: Subject to any disclaimer, the term of this patent is extended or adjusted under 35 U.S.C. 154(b) by 371 days.

(21) Appl. No.: 12/678,274

(22) PCT Filed: Nov. 7, 2008

(86) PCT No.: PCT/US2008/012586
§ 371 (c)(1),
(2), (4) Date: Mar. 15, 2010

(87) PCT Pub. No.: WO2009/078897
PCT Pub. Date: Jun. 25, 2009

(65) Prior Publication Data
US 2010/0204495 A1    Aug. 12, 2010

Related U.S. Application Data

(60) Provisional application No. 61/007,734, filed on Dec. 14, 2007.

(51) Int. Cl.
*B01J 19/26* (2006.01)
*C07D 301/08* (2006.01)

(52) U.S. Cl. .......................... 422/224; 549/523

(58) Field of Classification Search .............. 549/523; 422/224
See application file for complete search history.

(56) References Cited

U.S. PATENT DOCUMENTS

| | | | |
|---|---|---|---|
| 2,614,616 A | 10/1952 | Villoresi et al. | |
| 2,981,747 A | 4/1961 | Lang et al. | |
| 2,998,465 A | 8/1961 | Drummond et al. | |
| 3,081,818 A | 3/1963 | Braconier et al. | |
| 3,237,923 A | 3/1966 | Turner | |
| 3,518,284 A | 6/1970 | Foster | |
| 3,570,471 A | 3/1971 | Lazaridis | |
| 3,702,619 A | 11/1972 | Son | |
| 3,706,534 A | 12/1972 | Verheul et al. | |
| 4,012,469 A | 3/1977 | Accortt | |
| 4,256,604 A | 3/1981 | Aida et al. | |
| 4,348,476 A | 9/1982 | Hou | |
| 4,390,346 A | 6/1983 | Cramer et al. | |
| 4,393,817 A | 7/1983 | Lindberg | |
| 4,415,508 A | 11/1983 | Aida et al. | |
| 4,564,298 A | 1/1986 | Gritters et al. | |
| 4,573,803 A | 3/1986 | Gritters et al. | |
| 4,634,459 A | 1/1987 | Pischinger et al. | |
| 4,926,620 A | 5/1990 | Donle | |
| 5,037,619 A | 8/1991 | Alagy et al. | |
| 5,178,654 A | 1/1993 | Cowley et al. | |
| 5,250,267 A | 10/1993 | Johnson et al. | |
| 5,328,359 A | 7/1994 | Retallick | |
| 5,336,791 A | 8/1994 | Jennings et al. | |
| 6,231,648 B1 | 5/2001 | Marlowe | |
| 6,657,079 B1 | 12/2003 | Mitsumoto et al. | |
| 6,713,036 B1 | 3/2004 | Vanden Bussche et al. | |
| 6,840,256 B1 | 1/2005 | Ryan et al. | |
| 6,953,495 B2 | 10/2005 | Schwab | |
| 7,108,838 B2 | 9/2006 | McGee | |
| 2003/0021182 A1 | 1/2003 | Illy et al. | |
| 2003/0175183 A1 | 9/2003 | Guetlhuber | |
| 2004/0062689 A1 | 4/2004 | Gauthier et al. | |
| 2006/0036106 A1 | 2/2006 | Mazanec et al. | |
| 2006/0231645 A1 | 10/2006 | Chan | |

FOREIGN PATENT DOCUMENTS

| | | |
|---|---|---|
| DE | 102005020942 | 11/2006 |
| EP | 0006734 | 1/1980 |
| EP | 0026827 | 4/1981 |
| EP | 1705167 | 9/2006 |
| EP | 1726355 | 11/2006 |
| GB | 672446 | 5/1952 |
| GB | 705176 | 3/1954 |
| GB | 1262436 | 2/1972 |

(Continued)

OTHER PUBLICATIONS

Mawhinney et al, Halon Options Technical WorkingConference, p. 215-226 (2000).*

(Continued)

*Primary Examiner* — Bernard Dentz
(74) *Attorney, Agent, or Firm* — McDonnell Boehnen Hulbert & Berghoff LLP

(57) ABSTRACT

A hydrocarbon-containing gas is mixed with an oxygen-containing gas in a gas mixer in the presence of a water mist. The water mist surrounds and contacts entrained particles in either the oxygen-containing gas stream or the hydrocarbon-containing gas stream. The water acts to suppress and prevent ignition of the hydrocarbon gas in the mixer by serving as a sink for heat created by energetic collisions between such particles and structures within the gas mixer. The water mist also acts to quench ignition caused by such collisions. The water mist can be introduced into the gas mixer in a number of different configurations, including via nozzles injecting a mist into a hydrocarbon gas manifold or an oxygen gas manifold, nozzles placed within the gas mixer adjacent to ends of the oxygen supply pipes, and nozzles placed coaxially within the oxygen supply pipes in the gas mixer.

5 Claims, 3 Drawing Sheets

FOREIGN PATENT DOCUMENTS

| | | |
|---|---|---|
| GB | 1368922 | 10/1974 |
| GB | 2009174 | 6/1979 |
| GB | 2357318 | 6/2001 |
| JP | 55061927 A | 5/1985 |
| JP | 55064579 A | 5/1985 |
| TW | 590803 | 6/2004 |
| WO | WO01/85873 | 11/2001 |
| WO | WO2007/045457 | 4/2007 |
| WO | WO2009/078898 | 6/2009 |
| WO | WO2009/078899 | 6/2009 |
| WO | WO2009/078900 | 6/2009 |
| WO | WO2009/102311 | 8/2009 |

OTHER PUBLICATIONS

Burkholz, Armin, "Droplet Separation", 1989, pp. 180-182, VCH Publishers, New York, NY.

Communication pursuant to Article 94(e) EPC from European Patent Office re Application No. 08 862 808.6-2104, Feb. 10, 2011.

U.S. Appl. No. 12/678,257, Low Shear Gas Mixer, filed Mar. 15, 2010.

U.S. Appl. No. 12/678,263, Wet Scrubbing for Removing Particulate Solids From Oxygen Supply Line, filed Mar. 15, 2010.

U.S. Appl. No. 12/678,270, Oxygen/Hydrocarbon Rapid (High Shear) Gas Mixer, Particularly for the Production of Ethylene Oxide, filed Mar. 15, 2010.

U.S. Appl. No. 12/678,276, Hydrocarbon/Oxygen Industrial Gas Mixer With Coarse Water Droplet Environment to Reduce Ignition Potential, filed Mar. 15, 2010.

PCT International Preliminary Report on Patentability, PCT International Application No. PCT/US2008/012716, mailed Jun. 24, 2010.

PCT International Preliminary Report on Patentability, PCT International Application No. PCT/US2008/012714, mailed Jun. 24, 2010.

PCT International Preliminary Report on Patentability, PCT International Application No. PCT/US2008/012715, mailed Mar. 29, 2010.

PCT International Search Report, PCT International Application No. PCT/US2008/012587, mailed Feb. 10, 2009.

PCT International Search Report, PCT International Application No. PCT/US2008/012716, mailed Oct. 5, 2009.

PCT International Search Report, PCT International Application No. PCT/US2008/012715, mailed Feb. 3, 2009.

PCT International Search Report, PCT International Application No. PCT/US2008/012714, mailed Mar. 10, 2009.

PCT International Search Report, PCT International Application No. PCT/US2008/012586, mailed Feb. 11, 2009.

PCT Written Opinion, PCT International Application No. PCT/US2008/012587, mailed Feb. 10, 2009.

PCT Written Opinion, PCT International Application No. PCT/US2008/012716, mailed Oct. 5, 2009.

PCT Written Opinion, PCT International Application No. PCT/US2008/012715, mailed Nov. 19, 2009.

PCT Written Opinion, PCT International Application No. PCT/US2008/012714, mailed Mar. 10, 2009.

PCT Written Opinion, PCT International Application No. PCT/US2008/012586, mailed Feb. 11, 2009.

PCT International Preliminary Report on Patentability, PCT International Application No. PCT/US2008/012587, mailed Feb. 22, 2010.

PCT International Preliminary Report on Patentability, PCT International Application No. PCT/US2008/012586, mailed Feb. 22, 2010.

U.S. Appl. No. 12/678,257, Office Action mailed Mar. 16, 2012.

U.S. Appl. No. 12/678,270, Office Action mailed Jul. 12, 2012.

U.S. Appl. No. 12/678,276, Office Action mailed May 15, 2012.

U.S. Appl. No. 12/678,257, Response to Office Action mailed Mar. 16, 2012, filed Jun. 15, 2012.

U.S. Appl. No. 12/678,257, Office Action mailed Aug. 17, 2012.

Mawhinney et al., Halon Options Technical Working Conference, Protecting Against Vapor Explosions With Water Mist, 215-226, May 2-4, 2000.

U.S. Appl. No. 12/678,276, Response to Office Action mailed May 15, 2012, filed Aug. 15, 2012.

* cited by examiner

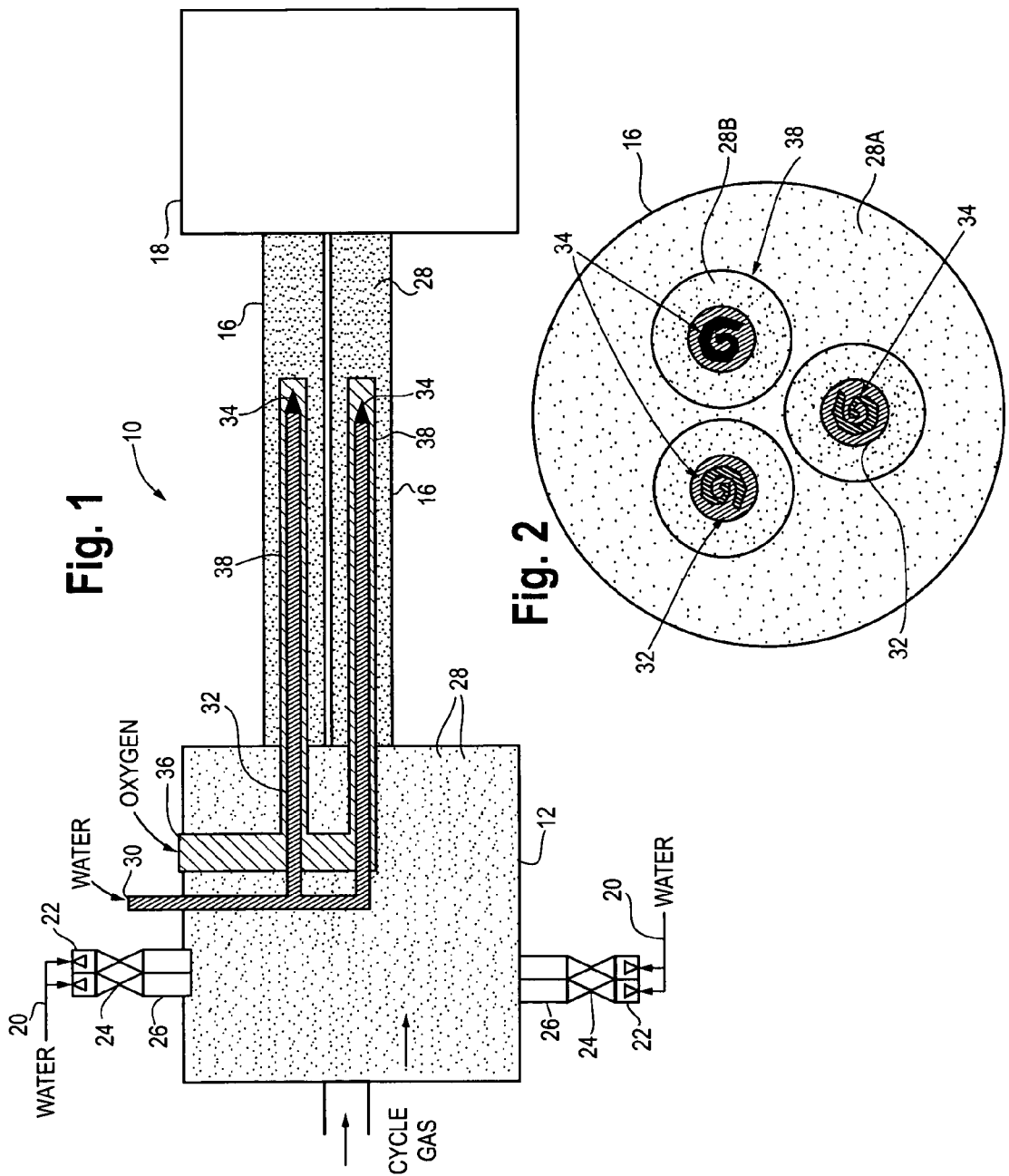

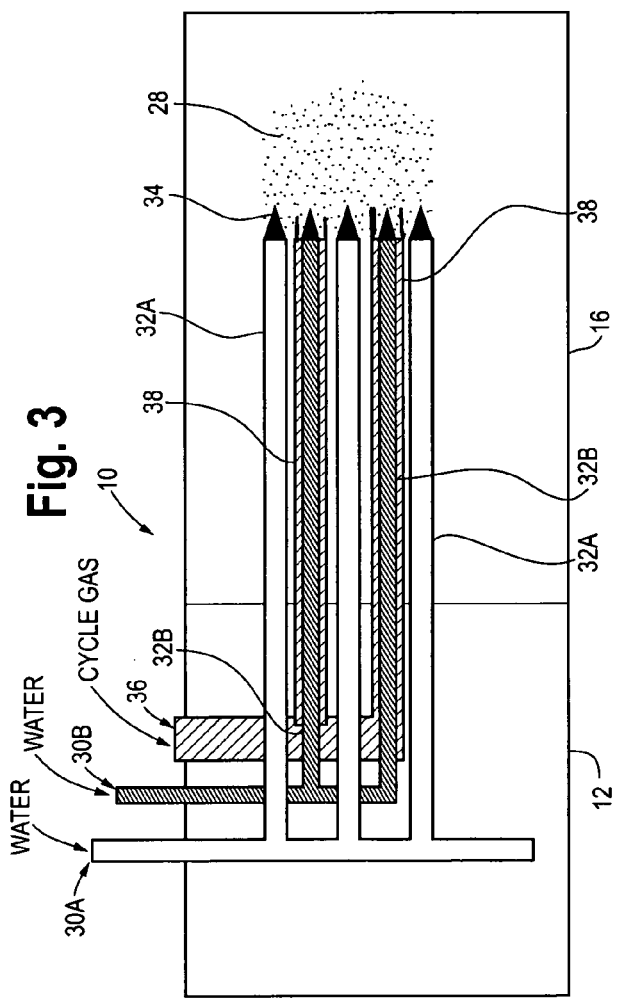
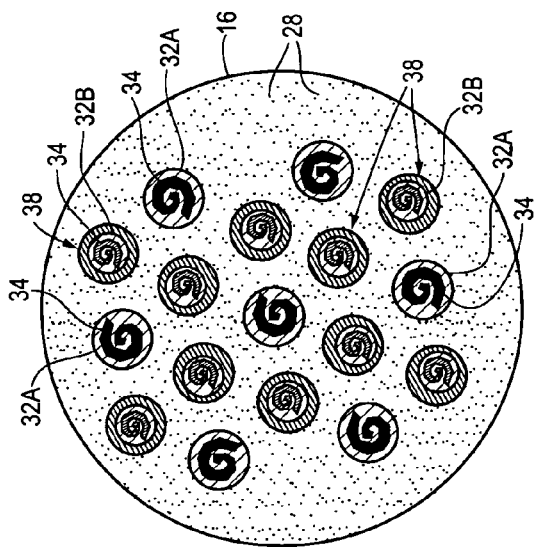

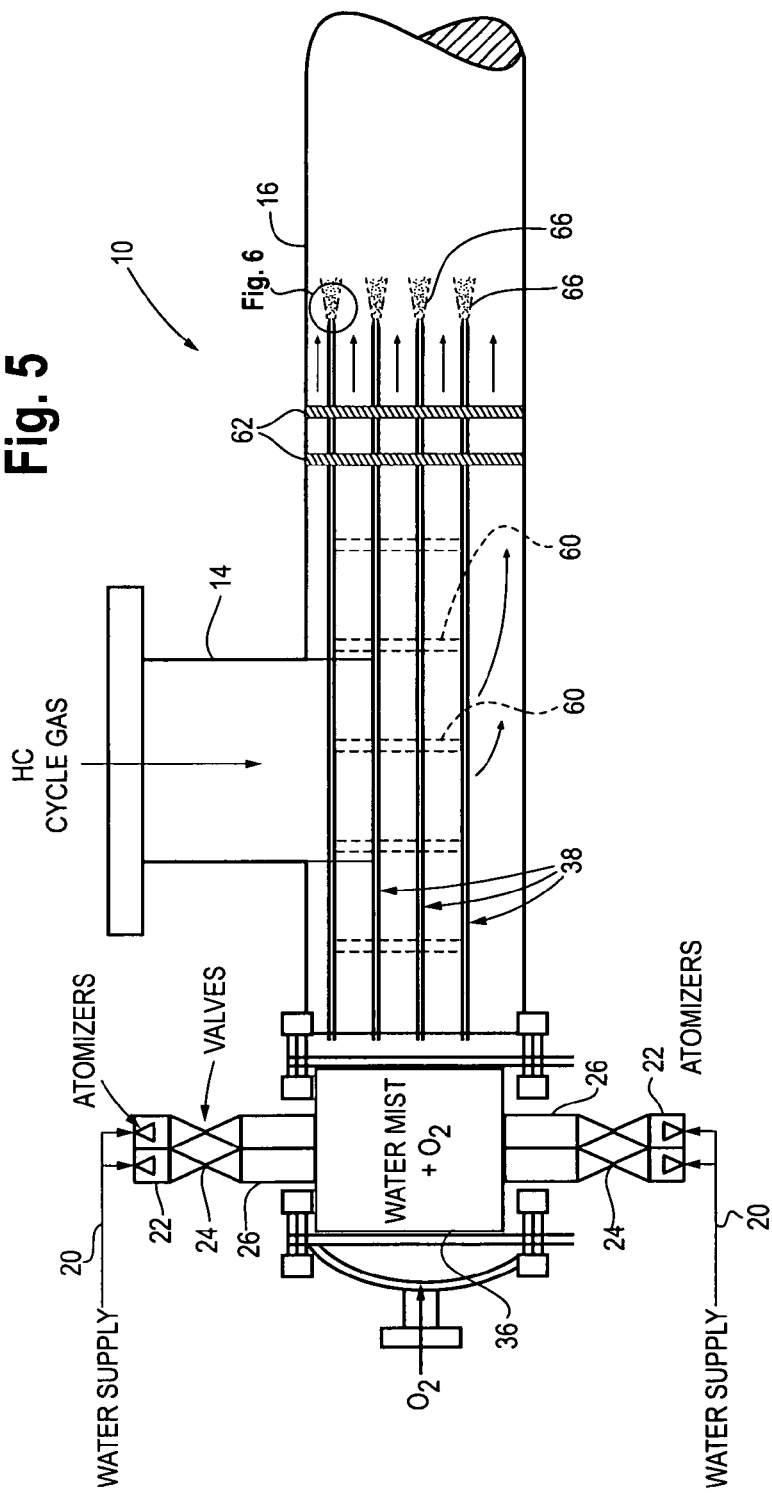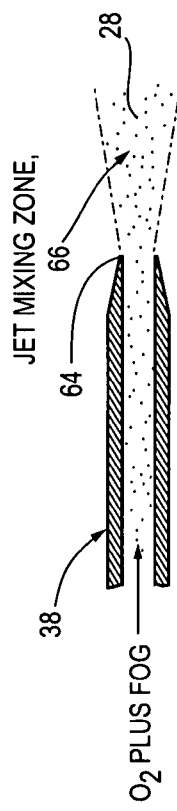

HYDROCARBON/OXYGEN INDUSTRIAL GAS MIXER WITH WATER MIST

CROSS-REFERENCE TO RELATED APPLICATIONS

This application is a U.S. National Phase of International Application No. PCT/US2008/012586, filed Nov. 7, 2008, which claims priority to U.S. Provisional Application No. 61/007,734, filed Dec. 14, 2007, all of which are herein incorporated by reference in their entirety.

BACKGROUND

This invention relates generally to gas mixers used in systems for gas-phase partial oxidation of hydrocarbon-containing gases. An example of where this invention has utility is systems for industrial production of ethylene oxide.

The chemical compound ethylene oxide (chemical formula $C_2H_4O$) is an important industrial chemical used as an intermediate in the production of ethylene glycol (the main component of automotive antifreeze) and other chemicals. Ethylene oxide is also used as a sterilant for foods and medical supplies. It is a colorless flammable gas at room temperature, and can be cooled and stored as a liquid.

Ethylene oxide first achieved industrial importance during World War I as a precursor to both ethylene glycol and the chemical weapon mustard gas. In 1931, Theodore Lefort, a French chemist, discovered a means to prepare ethylene oxide directly from ethylene and oxygen, using silver as a catalyst. Since 1940, almost all ethylene oxide produced industrially has been made using this method.

In current industrial processes, ethylene oxide is produced when ethylene ($CH_2=CH_2$) and oxygen ($O_2$) react on a silver catalyst at 200-300° C. showing large Ag nanoparticles supported on Alumina. Typically, chemical modifiers such as chlorine are also included. Pressures used are in the region of 1-2 MPa. The chemical equation for this reaction is:

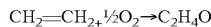

$$CH_2=CH_{2+}\tfrac{1}{2}O_2 \rightarrow C_2H_4O$$

In ethylene oxide production systems, a gas mixer is used to mix the hydrocarbon and oxygen gas streams just upstream of the reaction chamber where the silver catalyst is present. The gas mixer is typically constructed in the form of a vessel or pipe. The vessel includes an inlet manifold for each of the two gases. The vessel is sometimes constructed with a main outer pipe containing the hydrocarbon gas stream and internal concentric tubes or "fingers" which contain the oxygen stream. Mixing occurs at the point where the internal tubes end, where the oxygen gas flowing out of the fingers meets the main stream of hydrocarbon gas flowing in the outer tube. This basic design is described in U.S. Pat. No. 3,706,534.

The art has long recognized that there is a risk of ignition of a hydrocarbon-containing gas stream (e.g., a stream of gas containing for example ethylene mixed with other hydrocarbon gases) at the point where it is combined with an oxygen gas in a gas mixer. Ignition can occur when a particle (e.g. a piece of sand, rust or pipe scale) entrained in the hydrocarbon or oxygen gas stream strikes a metallic surface in the mixer, e.g., the wall of the mixer, thereby producing a spark. If the spark occurs in the hydrocarbon stream in the highly flammable zone e.g., at, or close to, the point of mixing of the two gas streams, ignition can occur. The ignition damages the gas mixer and also requires an interrupt of production to suppress the ignition and allow the gas mixer to cool before recommencing production. The flammable region is confined to the mixing zone of the two gases. The hydrocarbon-containing gas as well as the reactor feed blend are below the lower $O_2$ flammability limit—i.e., too rich to burn.

The art has devised a variety of gas mixer designs. Some of the designs are specifically directed to reducing the risk of ignition of hydrocarbon and oxygen gas stream. The known prior art includes the following patent documents, in addition to the above-cited '534 patent: U.S. Pat. No. 4,573,803; U.S. Pat. No. 3,702,619; U.S. Pat. No. 4,256,604; U.S. Pat. No. 4,415,508; U.S. Pat. No. 6,657,079; U.S. 2003/0021182; U.S. Pat. No. 3,518,284; U.S. Pat. No. 4,390,346; U.S. Pat. No. 3,237,923; U.S. Pat. No. 3,081,818; U.S. Pat. No. 2,614,616 and U.S. Pat. No. 6,840,256.

Other prior art of interest include British patents GB 705, 176 and 2,357,318; U.S. Pat. No. 5,336,791; and U.S. Pat. No. 4,393,817.

SUMMARY

In a first aspect of this disclosure, industrial production systems for gas-phase partial oxidation of a hydrocarbon-containing gas are disclosed which use a method for mixing the hydrocarbon-containing gas with an oxygen-containing gas. The method includes providing a gas mixer for mixing the oxygen-containing gas with the hydrocarbon-containing gas, introducing a water mist into the gas mixer, and mixing the oxygen gas and the hydrocarbon-containing gas in the presence of the water mist. The invention can be applied to hydrocarbon-air mixers and hydrocarbon-enriched air mixers. Hence, the term "oxygen-containing gas" is intended to encompass a stream of a gas containing oxygen generally, such as for example a stream of pure or substantially pure oxygen gas, a stream of air, or a stream of air which is enriched with oxygen gas.

In another aspect, an improvement to a gas mixer for an industrial production system for gas-phase oxidation of a hydrocarbon-containing gas is provided. The improvement is providing a means for producing a water mist in the gas mixer wherein the oxygen-containing gas and the hydrocarbon-containing gas are mixed in the gas mixer in the presence of the water mist. Several examples of the means for producing the water mist are described, including atomizers (nozzles) which inject a water mist into a hydrocarbon gas manifold, nozzles which inject a water mist into an oxygen gas manifold, and water pipes with mist-producing nozzles at the ends thereof either (1) concentrically located within oxygen pipes supplying oxygen in the gas mixer, (2) positioned along side the oxygen pipes, or both (1) and (2).

BRIEF DESCRIPTION OF THE DRAWINGS

FIG. 1 is a schematic representation of a gas mixer for an industrial production system for gas-phase oxidation of a hydrocarbon-containing gas, showing a first embodiment of a means for introducing a water mist into the gas mixer in the form of (1) atomizers (nozzles) which inject a water mist into a hydrocarbon gas manifold and (2) water pipes with mist-producing nozzles at the ends thereof concentrically located within oxygen pipes supplying oxygen to the gas mixer.

FIG. 2 is an end view of the one of the pipes carrying the hydrocarbon-containing gas shown in FIG. 1, showing the water pipes within the oxygen pipes and the mist provided by the atomizers and the nozzles at the end of the water pipes.

FIG. 3 is an illustration of a second embodiment of a gas mixer which features water pipes carrying water and nozzles at the end thereof which produce a mist at the mixing point where oxygen and hydrocarbon-containing gases are mixed.

FIG. 4 is an end view of the gas mixer of FIG. 3 showing the water pipes placed both adjacent to the oxygen pipes and concentrically within the oxygen pipes.

FIG. 5 is an illustration of a third embodiment of a gas mixer which features atomizing nozzles injecting a water mist into an oxygen gas manifold.

FIG. 6 is a detailed cross-section of the ends of the oxygen pipes of FIG. 5.

DETAILED DESCRIPTION

In industrial production systems for gas-phase partial oxidation of a hydrocarbon-containing gas, such as production of ethylene oxide, the mixing of hydrocarbon and oxygen gases in a safe, reliable manner is a continuing problem, particularly when the gases to be mixed may go through a flammable zone in the mixing process. The features of this disclosure provide improvements to a gas mixer and method of mixing gases which minimizes the probability of ignition. The mixing of the two gases is performed in a water mist environment.

Several different embodiments of a gas mixer featuring apparatus for producing the water mist environment will be described in some detail below. These embodiments illustrate applications suitable for ethylene oxide production in a gas mixer featuring low shear co-axial gas mixing. However, variation from the disclosed embodiments is of course possible and the invention can be practiced in a high shear gas mixer, such as described in WO 2009/078899, entitled Oxygen/Hydrocarbon Rapid (High Shear) Gas Mixer, Particularly For The Production Of Ethylene Oxide, the entire content of which is incorporated by reference herein. In the low shear embodiments, a water mist is injected coaxially in one gas stream, particularly a high-purity oxygen feed, and/or alternatively surrounding one gas stream at the point of entry into the second gas stream, particularly the mixing of a high-purity oxygen stream into a hydrocarbon-containing gas stream.

The purpose of the water mist environment is to reduce the probability of ignition of the flammable gas envelope where the two gases initially mix, or to quench an ignition should one initiate, by introducing a sufficient quantity of small water droplets into the gas stream at the point of the high flammability gas envelope so as to provide enhanced mixing, wetting of the surface of any entrained particles in either the hydrocarbon stream or the oxygen stream, and a heat sink to transfer any heat generated from particle impact or particle fracture while the particle is still present in the flammable region of the flammable gas stream. In general, the gas mixer features atomizers (water mist producing nozzles) which are designed to produce the water droplet having a size approximately ≦200 microns SMD (Sauter Mean Diameter). This term is defined as the drop diameter that has the same surface area to volume ratio as the entire spray. However, the droplets could be considerably smaller, such as for example as small as 1 micron. At elevated pressures, such as found in the gas mixers of the type of this disclosure, the water mist may act like a dense gas which travels with the oxygen gas into the high flammability zone and act as an ignition suppressant. Materials for construction of the gas mixer and the mist/fog generating devices may be stainless steel, Monel, Inconel, or other corrosion and ignition resistant metal. Such metals may also be used in the highest velocity zones and the gas-distributing pipes.

One application of the invention is direct oxidation ethylene oxide process mixers, which mix oxygen at intermediate pressure (~20 bar) with recycled hydrocarbon gas containing ethylene and other gases. Oxygen pressures run around ~26 bar. The invention can similarly be used for other partial oxidation processes using pure oxygen or enriched air.

The features of this disclosure redefines the oxygen/hydrocarbon mixing process to reduce the potential for ignition in the high flammable gas envelope that exists for some distance downstream of the point of injection of oxygen into the hydrocarbon-rich stream prior to complete mixing of the oxygen-hydrocarbon stream. The invention accomplishes this by mixing the gases in the presence of a fine water mist, and most preferably in the presence of a droplet size of 1-15 micron SMD, which behaves as a dense gas, to provide a heat sink to dissipate the impact energy of entrained particles in either the hydrocarbon or oxygen gas streams or to quench an ignition should one occur. The invention is particularly useful for mixing oxygen into the recycle gas containing ethylene in an ethylene oxide process.

The methods and gas mixer of this disclosure differs from prior technology in that it introduces a fine water mist directly and concurrently into either or both of the oxygen and hydrocarbon streams. Ideally, the mist is formed from water droplets at or less than 200 microns in size to wet the surface of any particles traveling with the gas stream(s) to reduce the energy of impact of the wet particle on mixing device wall and/or act as an ignition suppressant. Water injection for the purpose of flame suppression is commonly employed in a variety of applications like turbine engines and oil well fires, however, no applications of the type described have been found that specifically both minimize the occurrence of ignition sources and suppress the growth of an incipient flame.

The features of this disclosure satisfy a long-felt need in the art in that it allows for the injection of oxygen into a hydrocarbon-rich gas stream while minimizing the probability of igniting the mixture. The advantage is particularly significant for a range of application in which gas mixing occurs at elevated pressures (e.g. 20 bar), which are commonly found in partial oxidation processes such as ethylene oxide production.

EXAMPLE 1

FIG. 1 is a schematic representation of a gas mixer featuring a water mist environment where the hydrocarbon-containing gas and oxygen-containing gases meet. The gas mixer 10 includes a hydrocarbon gas manifold 12 receiving recycled gas containing hydrocarbons such as ethylene from a source along an inlet pipe 14. Although ethylene is the hydrocarbon gas of commercial interest in Example 1, it is typically controlled to about 20-35% by volume within a ballast gas such as methane or nitrogen. One or more pipes 16 are connected to the hydrocarbon gas manifold 12. Gas mixing occurs in the pipes 16. The pipes function as mixing chambers for the gas mixer 10. Mixed gases are collected in a second manifold 18.

The gas mixer 10 features a means for producing a water mist in the pipes 16. In particular, water supply lines 20 are provided which supply water to atomizers 22. The atomizers 22 produce a fine water mist. In one embodiment, the atomizers are designed to produce water droplets of a size of about 200 microns or less. Valves 24 are placed downstream of the atomizers 22. Tubes 26 carry mist produced by the atomizers 22 are mounted in the hydrocarbon gas manifold 12. Thus, a fine mist or fog is produced in the hydrocarbon gas manifold 12, droplets being indicated at 28. The mist created in the manifold 12 is mixed and carried into the pipes 16 and thus is present in the hydrocarbon-containing gas stream in the pipes 16.

Oxygen is supplied to the gas mixer via an oxygen gas manifold 36. Oxygen pipes 38, sometimes referred to in the art as "fingers", are connected to the manifold 36. The oxygen pipes 38 are located within the hydrocarbon pipes 16. Oxygen flows into the pipes 38 from the manifold 36 and flows out the distal open end of the pipes 38.

The mixer 10 further includes a water manifold 30 connected to a water source which supplies water to the proximal end of water mist pipes 32. Each of the hydrocarbon pipes 16 has one or more oxygen pipes 38 placed within it, and each oxygen pipe has a water mist pipe 32 coaxially within it, as shown in FIG. 1. A nozzle 34 is placed at the distal end of the pipes 32. The nozzle 34 is preferably a pig-tail type nozzle which produces a cone of fine water droplets. Alternatively, the nozzle is a hollow cone pressure swirl nozzle. The tip of the nozzle 34 is positioned either adjacent to, or slightly inward from the distal end of the oxygen pipe 38, as shown in FIG. 1.

In operation, hydrocarbon-containing gas enters manifold 12 where it is divided into one or more independent pipes 16. An oxygen-containing stream, preferably pure oxygen, enters manifold 36 where the stream is divided into one or more pipes 38, smaller than and concentric with pipes 16. Concentric pipes 38 extend some distance down the outer pipe 16 as determined by engineering calculations to be optimal for mixing and separation of the mixing zone where the oxygen-containing gas mixes with the hydrocarbon-rich gas. In addition, a water stream enters manifold 30. The manifold 30 could be positioned inside the oxygen manifold 36. The manifold 30 is connected to the proximal ends of one or more water pipes 32. The water pipes 32 are smaller in diameter and concentrically located within the oxygen pipe 38, which are concentric in pipes 16. Each oxygen pipe 38 has one water pipe 32 located within it. At the end of pipes 32 are affixed atomizing nozzles 34 designed for producing a fine water mist having a droplet size of approximately 200 microns or less. The nozzle 34 at the end of pipe 32 terminates approximately coincident with the end of pipe 38 and before the end of pipe 16 so as to cause the oxygen-containing gas to pass through a fine water mist as it mixes with the hydrocarbon-rich gas in the pipe 16.

As noted above, in addition to the water mist injected into the oxygen stream, water is introduced into the hydrocarbon manifold 12 through one or more atomizing nozzles 22 such that a fine water mist mixes with the hydrocarbon stream. Particles traveling with either gas stream are wetted by the mist, reducing the impact energy of the particle if it were to strike a surface of either pipe 16 or pipe 38. The mist also enhances heat transfer away from the particle and quenches an ignition, if one should occur. The oxygen/water/hydrocarbon-containing gas mixture is re-gathered in manifold 18 for transfer to downstream water removal processing station, prior to entering a reactor located further downstream.

FIG. 2 is an end view of the one of the pipes 16 carrying the hydrocarbon-containing gas shown in FIG. 1 with mist (indicated by droplets 28A) present in the hydrocarbon-containing gas stream. The Figure also shows the water pipes 32 coaxially located within the oxygen pipes 38 and the mist 28B provided by the nozzles 34 located at the end of the water pipes 32. While in FIG. 2 there are three oxygen pipes per hydrocarbon pipe 16, this may of course vary, e.g., depending on the size and number of hydrocarbon pipes 16 in the gas mixer.

The downstream water removal processing station may use a pressure vessel column to coalesce water out of the mixed gas stream. For example, this vessel could be an integral part of the $CO_2$ removal column, which is nearby in a typical processing scheme. The recovered water may be filtered to remove particulate matter and recycled back into the water supplies of FIG. 1.

The nozzles 34, like the atomizers 22 of FIG. 1, are also designed to produce a droplet size of approximately 200 microns or less SMD. In one possible embodiment, the nozzles 34 and/or 22 are designed to produce water droplets of a size of 1-20 microns SMD, whereby a micron-sized droplet mist is produced.

In a variation to the embodiment of FIG. 1, the water pipes 32 are positioned in the pipes 16 but not within the oxygen pipes. Rather, the water pipes are positioned adjacent to the oxygen pipes 38 such that the nozzles 34 at the end of the water pipes 32 direct a water mist into the mixing zone where oxygen gas is mixed with the hydrocarbon-containing gas in the pipes 16.

EXAMPLE 2

FIG. 3 is a schematic illustration of a second example of a gas mixer incorporating the water mist features of this invention.

In this embodiment the hydrocarbon-rich gas is supplied from a manifold to a single vessel or pipe 16 which functions as a mixing chamber for the gas mixer 10. In this embodiment, the hydrocarbon-containing gas is not separated into multiple parallel pipes such as pipes 16 in the previous embodiment, but rather flows around one or more oxygen-carrying pipes 38 positioned within the vessel 16. As in Example 1, oxygen-containing gas, preferably high purity oxygen, enters manifold 36 where the stream of gas is divided into one or more pipes 38. The oxygen pipes have a distal open end through which oxygen gas flows out of the oxygen pipes 38.

The gas mixer 10 features a means for producing a water mist in the pipe or vessel 16. In particular, water enters manifold 30A where it is divided into pipes 32A. The pipes 32A have a nozzle 34 at the end thereof for producing a water mist having a droplet size smaller than about 200 microns SMD. Water also enters a water manifold 30B where it is divided into multiple water mist pipes 32B, which are smaller than and concentrically located in the oxygen pipes 38. At the end of pipes 32B are affixed atomizing nozzles 34 capable of producing a fine water mist having droplet sizes smaller than about 200 microns. The nozzles 34 at the end of pipes 32B terminate coincident with the end of pipe 38 so as to cause the oxygen-containing gas to pass through a fine water mist as it mixes with the hydrocarbon-rich gas. The water pipes 32A are closely adjacent and parallel to oxygen pipes 38 and interspersed between pipes 38 in a pattern such as shown in FIG. 4. One water mist generating pipe 32A is provided for every three or four oxygen injection pipes 38.

Particles traveling with either gas stream are wetted by a mist, reducing the impact energy of the particle if it were to strike a surface of either pipe 32, 38 or vessel 16. The oxygen/water/hydrocarbon-containing gas mixture is transferred to downstream water removal equipment, prior to entering a reactor located further downstream. The use of multiple water atomizers in this embodiment improves operating reliability of the system.

EXAMPLE 3

A third embodiment of this invention is shown in FIG. 5. In this embodiment, oxygen gas is supplied to an oxygen gas manifold 36. Hydrocarbon-containing gas is supplied via an inlet 14 to a pipe 16 which functions as a mixing chamber in the gas mixer.

The gas mixer 10 features a means for producing a water mist in the pipe 16. In this embodiment a fine water mist, preferably with a droplet size at or below about 200 microns, is generated in the oxygen manifold 36 by a series of two or more atomizing nozzles 22 connected to a water supply 20. The nozzles 22 are arranged around the circumference of the manifold 36 and inject a water mist into the manifold 36. Valves 24 and pipe segments 26 connect the nozzles 22 to the manifold 36. Oxygen enters the misty environment of manifold 36 where the wet oxygen-water mist is divided into one or more parallel oxygen pipes 38.

Hydrocarbon-rich gas enters the gas mixer 10 from the side inlet 14 and flows into the vessel 16 in a direction parallel to pipes 38. Flow straighteners 62 may be provided to provide axial flow of the hydrocarbon-containing gas. Properly designed, these serve to equalize the flow distribution of the cycle gas across the cross-section of the pipe 16. Supports 60 are provided to support the oxygen pipes 38 and prevent vibration of the pipes 38. The wet oxygen gas exits the distal open end of pipes 38 and mixes with the hydrocarbon-rich gas. Particles traveling with either gas stream are wetted by the mist, reducing the impact energy of the particle if it were to strike a surface of either the outer containment pipe 16 or oxygen pipes 38. The mist also enhances heat transfer away from the particle and quenches an ignition, if one should occur. The length of pipes 38 is determined to minimize residence time and reduce flow eddies. The distal end 64 of one of the oxygen pipes 38 is shown isolated and in cross-section in FIG. 6. The pipe 38 ejects an oxygen/water mist in a jet mixing zone 66 where the oxygen gas is mixed with hydrocarbon-containing gas flowing over the outer peripheral surface of the pipe 38.

Nozzles 22 are preferably designed to produce droplets having a size at or below approximately 200 microns SMD.

Suitable nozzles for the design of Examples 1-3 are pig-tail type nozzles, commercially available from BETE Fog Nozzle, Inc., Greenfield, Mass., or Spraying Systems Co., Wheaton Ill. Other nozzles may be used, including spiral pintle, hollow cone pressure swirl, and ultrasonic atomizing nozzles.

In one embodiment, the temperature of the water used to produce the water mist is at ambient temperature. In an alternative embodiment, the water is heated above ambient. For example, the water is heated to the temperature of the hydrocarbon-containing gas stream. In an EO production scenario, the temperature of the hydrocarbon recycle gas stream is typically between about 35-40 degrees C. and 65-70 degrees C. The water that is supplied to the spray nozzles can be either at ambient temperature, or water which has been heated to a temperature of between 35 and 70 degrees C.

While presently preferred embodiments have been described with particularity, variation from the specifics of the disclosed embodiments may be made without departure from the scope of the invention. All questions concerning scope of the invention are to be determined by reference to the appended claims.

We claim:

1. In an industrial production system for gas-phase partial oxidation of a hydrocarbon-containing gas, a method for mixing the hydrocarbon-containing gas with an oxygen-containing gas, comprising the steps of:
   providing a gas mixer for mixing the oxygen-containing gas with the hydrocarbon-containing gas;
   introducing a water mist into the gas mixer; and
   mixing the oxygen-containing gas and the hydrocarbon-containing gas in the presence of the water mist.

2. The method of claim 1, wherein the gas mixer includes a hydrocarbon gas manifold, and wherein the introducing step comprises the step of supplying the water mist to the hydrocarbon gas manifold.

3. The method of claim 1, further comprising the step of recovering water from the mixed hydrocarbon and oxygen gases.

4. In a gas mixer for an industrial production system for gas-phase partial oxidation of a hydrocarbon-containing gas, the improvement comprising:
   providing a means for producing a water mist in the gas mixer wherein the oxygen-containing gas and the hydrocarbon-containing gas are mixed in the gas mixer in the presence of the water mist.

5. The improvement of claim 4, wherein the gas mixer further comprises a hydrocarbon gas manifold, a water supply, a water mist producing device connected to the water supply and wherein the water mist producing device produces the water mist which is supplied to the hydrocarbon gas manifold.

* * * * *